(12) United States Patent
Swoyer

(10) Patent No.: US 7,957,818 B2
(45) Date of Patent: Jun. 7, 2011

(54) STIMULATION LEAD DESIGN AND METHOD OF MANUFACTURE

(75) Inventor: John M. Swoyer, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 238 days.

(21) Appl. No.: 12/492,645

(22) Filed: Jun. 26, 2009

(65) Prior Publication Data

US 2009/0326626 A1 Dec. 31, 2009

Related U.S. Application Data

(60) Provisional application No. 61/075,955, filed on Jun. 26, 2008.

(51) Int. Cl.
*A61N 1/00* (2006.01)
(52) U.S. Cl. ........................................ 607/116
(58) Field of Classification Search .................. 607/116, 607/117, 118, 119, 122, 126, 127, 2, 37, 607/4; 29/33 M; 439/668; 600/374, 381, 600/486
See application file for complete search history.

(56) References Cited

U.S. PATENT DOCUMENTS

| | | | |
|---|---|---|---|
| 4,280,511 A | 7/1981 | O'Neill | |
| 4,432,377 A | 2/1984 | Dickhudt | |
| 4,481,953 A | 11/1984 | Gold et al. | |
| 4,538,623 A | 9/1985 | Proctor et al. | |
| 5,458,629 A | 10/1995 | Baudino et al. | |
| 5,954,759 A | 9/1999 | Swoyer et al. | |
| 6,026,567 A | 2/2000 | Swoyer et al. | |
| 6,052,608 A | 4/2000 | Young et al. | |
| 6,144,870 A | 11/2000 | Griffin, III | |
| 6,181,971 B1 | 1/2001 | Doan | |
| 6,208,881 B1 | 3/2001 | Champeau | |
| 7,146,222 B2 | 12/2006 | Boling | |
| 2001/0025192 A1 | 9/2001 | Gerber et al. | |
| 2004/0249430 A1 | 12/2004 | Martinez et al. | |
| 2006/0265037 A1 | 11/2006 | Kuzma et al. | |
| 2007/0168004 A1 | 7/2007 | Walter | |
| 2008/0147158 A1 | 6/2008 | Zweber et al. | |
| 2008/0178449 A1 * | 7/2008 | Huotari et al. | ............... 29/33 M |

* cited by examiner

*Primary Examiner* — George Manuel
*Assistant Examiner* — Robert N Wieland
(74) *Attorney, Agent, or Firm* — Steven W. Winn; Michael F. Scalise

(57) ABSTRACT

The invention is an implantable electrical stimulation lead for chronic or long term use that has an improved electrical connection between the electrode and conductor. This is accomplished through the use of metal coils embedded in the sidewall of the lead body. A wire conductor providing electrical continuity from a proximal electrode to a distal electrode has a protruding portion extending through the sidewall. This protruding portion can reside adjacent to either a proximal or a distal electrode. In any event, the protruding portion of the lire is captured underneath a ring electrode that is physically deformed into direct contact with the metal of the wire, preferably by swaging. This serve to make electrical conductivity between the wire and the electrode with the embedded coil serving as support during the swaging process.

29 Claims, 6 Drawing Sheets

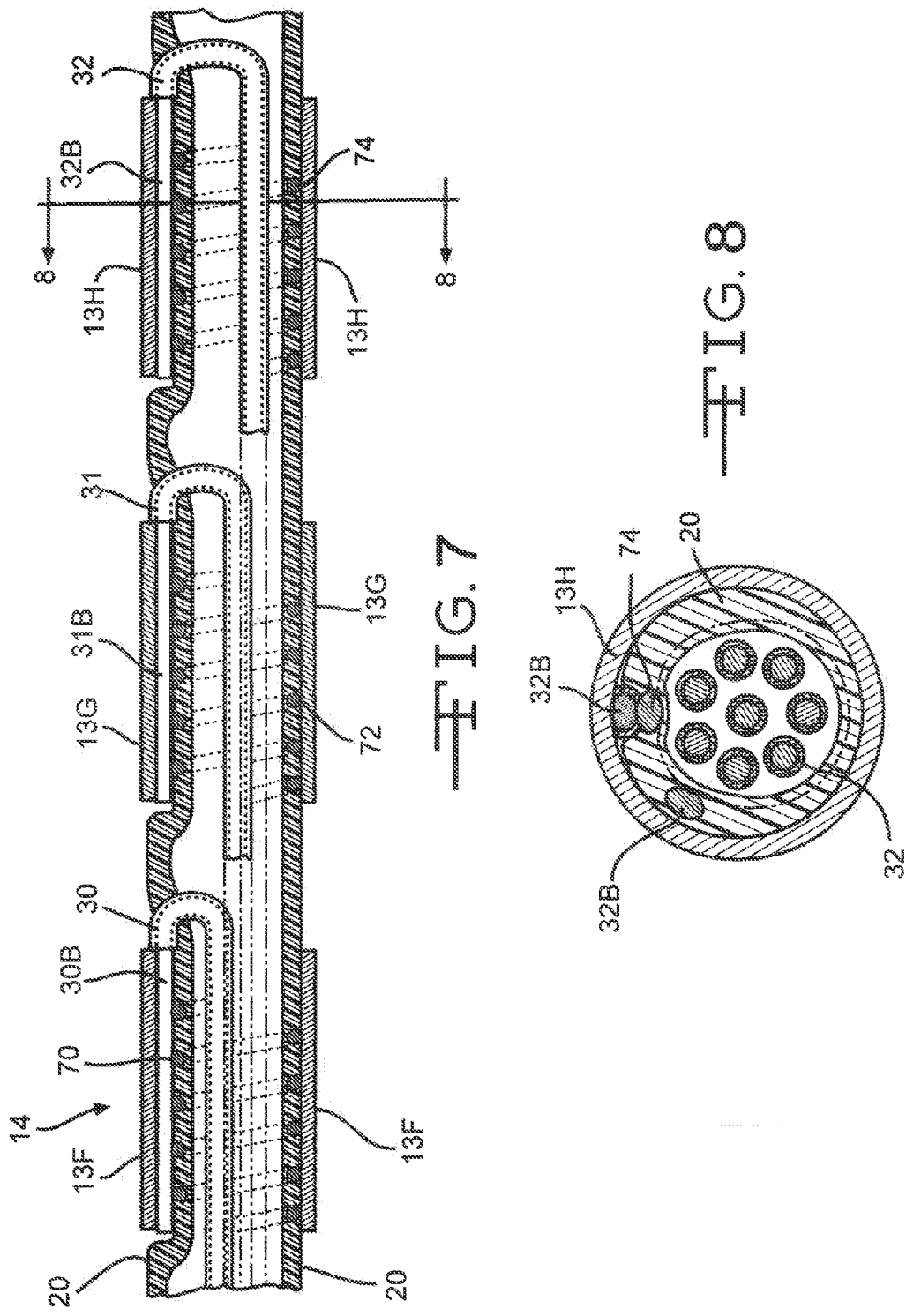

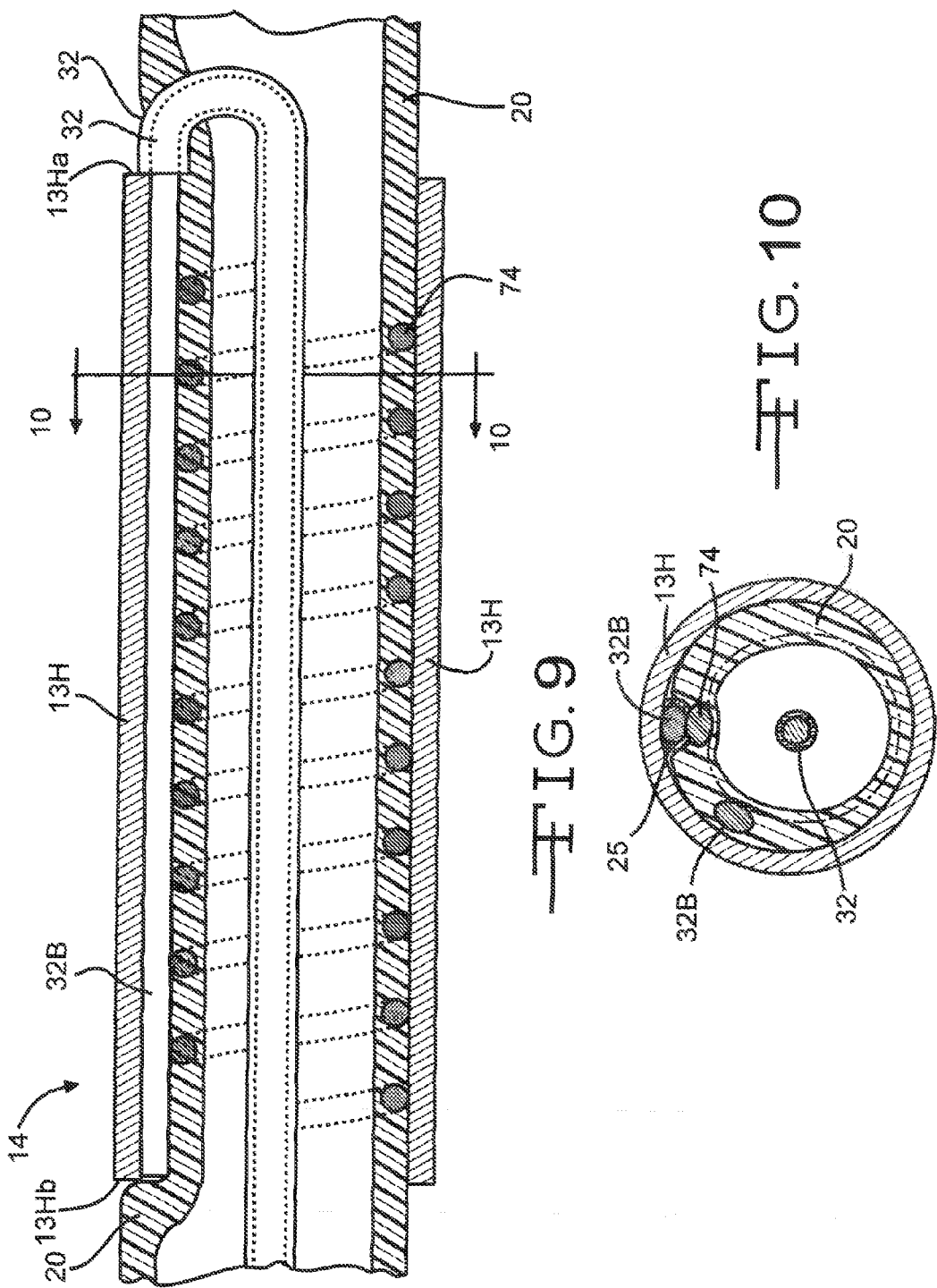

STIMULATION LEAD DESIGN AND METHOD OF MANUFACTURE

CROSS-REFERENCE TO RELATED APPLICATION

This application claims priority from U.S. Provisional Application Ser. No. 61/075,955, filed Jun. 26, 2008.

FIELD OF THE INVENTION

The present invention is related generally to implantable medical devices. More specifically, the present invention is related to implantable medical electrical leads.

BACKGROUND OF THE INVENTION

Implantable medical devices designed for patient pain management, also known as neuromodulation devices, have improved dramatically over the past few decades. These implantable medical devices provide much needed relief for patients who suffer from pain which emanates from the spine region. One of the key components of such devices is the implantable electrical stimulation lead. Some electrical stimulation leads, also referred to as percutaneous stimulation leads, are implanted into the patient by insertion of the electrical lead through the skin, through the ligamentum flavum, and into the epidural space or epidural potential space. The electrical lead can then be run along the spinal cord, over the dura membrane, without puncturing the dura membrane. As such, these leads are required to penetrate deep into narrow openings and passages inside the human body and are intended for long term or chronic use by the patient. Once inserted into the epidural space, the lead is intended to reside in the patient over a period of several years.

It is desirable to design an implantable lead to be as minimally invasive as possible because of the reduced risk of infection and improved recovery time of the patient. It is undesirable for the lead to be removed once inserted into the patient if, for example, the electrical lead becomes defective or inoperable. Removing an electrical lead creates additional stress for the patient and increases the risk of infection both when an electrical stimulation lead is removed as well as when a new electrical stimulation lead is implanted.

One such mode of failure in current implantable electrical stimulation leads is impaired electrical contact. Impaired electrical contact occurs when a section of the lead's polymer body becomes entrapped between the conductor wire of the lead and the outer electrode ring that is wrapped around or surrounds the electrical lead body. Such a problem can occur due to the cold flow of the polymer as it migrates between the conductor wire and the electrode ring. This problem is most concerning for chronic or long term implant electrical leads which can reside in a patient over many years.

Electro-physiological catheter leads are typically designed such that the electrode ring is swaged over a polymer cylindrical lead body and conductive wire. An interference fit between the electrode ring and conductor wire around the polymer lead body is created to produce the electrical contact. Delivery of electrical stimulation to the patient is dependent on the electrical connection between the electrode and the conductive wire, and is contingent on the interference fit of the swaged electrode ring over the conductor wire and the polymer lead body. Over time, the polymer of the electrical lead body can become "sandwiched" between the electrode and the conductor wire, which results in impaired electrical conduction between the electrode ring and conductor wire. As a result, the patient's electrical stimulation degrades or ceases.

This problem of impaired electrical contact between the conductor wire and lead body is a major concern for chronic or long term electrical stimulation leads. The problem of impaired electrical contact has been previously addressed through the use of crimping or welding the electrode ring surrounding the conductor wire of the polymer lead body.

In crimping, the electrode ring is pinched around the conductor wire and polymer lead body. This process requires the use of a metal insert or metal sleeve that is placed around the polymer lead body. The metal insert is used as a mechanical stabilizer for the polymer lead body that provides a solid rigid surface that protects the polymer lumen from deforming. The conductor wire is placed in contact between the outside surface of the metal insert and the inside surface of the electrode ring. The electrode ring and conductor wire assembly is then crimped or swaged around the lead body. In such prior art designs, the force of the crimping damages the polymer lead body; therefore requiring metal inserts to serve as a solid rigid protective barrier to the surface and structure of the polymer lead lumen. Further, the use of a sleeve or core insert in the crimping process adds additional width to the body of the electrical lead which is undesirable because it makes it more difficult for the electrical lead to penetrate deep within narrow passages of the human body. The use of a narrow electrical lead is more minimally invasive and minimizes undesirable stress and trauma to the patient.

The problem of impaired electrical contact between the conductor wire and lead body has also been previously addressed through the use of welding. Welding does not require additional crimping components such as a sleeve or core insert, but limits the use of available materials due to its excessive heat and undesirable material reactions that are inherit in the welding process. For example, welding will expose silver in silver cored wire, a commonly used material for use as a conductor; the exposed silver dissolves in the body which could result in bodily harm. Material migration into the body can further result in a weakened bond that increases the probability of a break in the conductor wire, resulting in impaired stimulation lead operation. If a break occurs, the electrical stimulation lead will need to be replaced; therefore requiring the patient to undergo an additional operation creating more unnecessary trauma and stress to the patient.

Accordingly, what is needed is a new chronic electrical stimulation lead that improves upon the previous crimping designs. The new electrical stimulation lead must also exhibit improved electrical contact stability without the material limitations of welding inherent in relatively narrow lead.

SUMMARY

The present invention provides an implantable medical electrical stimulation lead. Preferably, the lead is suitable for long term or chronic implantation use in the body. The lead is composed of an elongate hollow lumen or body having a length, a proximal portion, and a distal portion; at least one electrical conductor wire disposed inside the lumen; and at least one electrode, also referred to as an electrode ring, disposed around the outside surface of the lumen or lead body in the proximal and distal portions of the lead.

The proximal portion of the lead comprises at least one electrode connected to a conductor wire disposed inside the lead body. The proximal electrode serves as a contact around the outside surface of the lumen. Each individual conductor wire disposed inside the lead body is connected to at least two electrodes; one proximal electrode located in the proximal portion of the lead and a corresponding distal electrode located in the distal portion thereof. Preferably there are a plurality of conductor wires, each being in contact with one electrode within the series of electrodes in both the distal portion and proximal portion of the lead. For example, a conductor wire which is in electrical contact with the second electrode from the proximal end of the lead is preferably in electrical contact with the electrode that is second from the distal end thereof. Alternately, the second electrode from the proximal lead end might be in electrical contact with the electrode that is most proximal to it in the distal lead portion or any other electrode located in the distal lead portion. Likewise, a conductor wire might be in electrical contact with any electrode in the proximal portion of the lead. Multiple conductors can be disposed in the lead body, each of which is electrically connected to any one of a number of the proximal and corresponding distal electrodes. The proximal electrodes provide for connection to the medical device while the distal electrodes contact with the patient for the purpose of providing electrical stimulation from the medical device to a selected body tissue or nerve.

Connection between a conductor wire and an electrode, regardless whether the electrode is located at the proximal or distal lead portion, is created by protruding the conductor wire through the wall of the polymer lumen or lead body and placing the wire under the surface of the electrode. Preferably the electrode extends 360° annularly around the outer surface of the lumen or lead body.

Incorporated within the wall of the polymer lumen or lead body are coils which have an annular 360° extension within the polymer lumen or lead body. The coils are similar to wires in a spiral orientation. The coils provide a rigid structure to the wall of the polymer lumen or lead body under the electrode ring and conductor wire during the swaging process. In addition to providing improved rigidity to the polymer wall of the lumen, the coils provide pressure points that make physical contact against the conductor wire. This secures the conductor wire in place and retards the possible migration of the lumen polymer due to cold flow.

The electrodes in the proximal portion are in electrical contact with the implantable medical device through insertion of the proximal end in the medical device header or port. The electrical stimulation generated in the implantable medical device enters the electrical stimulation lead at the proximal portion through the proximal electrodes. The stimulating electrical energy is then conducted via the internal conductor wires to the distal portion of the lead. This electrical stimulation energy then exits the lead into the patient via the conduction of the electrode rings that are in the distal lead portion. The distal portion of the electrical stimulation lead is the portion of the lead that is positioned near the patient's spinal region or other body tissue to provide electrical stimulation therapy.

As previously mentioned, the problem with current implanted electrical leads is a propensity for the electrical connection between the conductor wire and electrode ring to degrade over time. One reason for this degradation of electrical conductivity is due to migration of the polymer from the lead body to between the electrode ring and conductor wire. The presence of polymer material there can create an interruption in the electrical continuity between the conductor wire and electrode ring, thus impairing the electrical stimulation to the patient.

In the present invention, however, the conductor wires reside inside the hollow opening of the polymer lead body. Each conductor wire individually traverses through the hollow lumen from the proximal portion to the distal portion. At these opposed end portions the conductor wire is advanced through an opening of the wall of the lead body and secured under a respective electrode ring. The length of that portion of a conductor wire that penetrates or protrudes through the wall of the lead is substantially the same as the length of the electrode ring. That way, the protruding portion of the conductor wire is fit under the electrode and is not exposed to the external environment. Instead, the entire protruding portion of the conductive wire is in contact with the inside surface of the electrode ring. Once the protruding portion of the conductor wire is inserted under the electrode ring, the conductor wire and electrode ring are swaged together, supported on the outer surface of the lead lumen. A series of metallic coils is embedded in the walls of the electrode lead body, one in the area of each electrode ring. The metallic coils provide added mechanical stability to the lead body during the swaging process as well as create a barrier to migration of the polymer material between the electrode ring and the conductor wire. In that respect, this new design provides increased electrical conduction stability through control of polymer migration in a manner that provides a more slender lead design that does not have material use restrictions.

The present invention also includes an insertion tool that or stylet is used to implant the lead into the desired location of the body. The insertion tool includes a handle supporting a solid tubular member comprised of distal and proximal tubular portions. The distal end of the insertion tool is placed inside the proximal end of the present electrical stimulation lead and advanced through the lead body to the distal portion thereof. Once the insertion tool is fully engaged inside the lead, the lead is inserted into the body and placed in the desired location. Once the desired location has been reached, the insertion tool is removed from the lead, leaving the stimulation lead in place. The proximal portion of the stimulation lead is then connected to a header of the medical device to complete electrical connection between the lead and the device. The medical device is then implanted in the desired location in the body.

DESCRIPTION OF THE DRAWINGS

FIG. 7 illustrates a cross sectional view, partially in elevation, of the present invention lead, which includes a series of conductor wires, hollow lead body, internal support coils, and electrode rings.

FIG. 8 depicts a cross sectional view taken along line 8-8 of FIG. 7.

FIG. 9 is an enlarged cross sectional view, partially in elevation, of the distal most electrode 13H shown in FIG. 7.*illustration* an exploded longitudinal cross section view of the invention which shows a hollow lead body, conductor wire, internal support coils and electrode ring.

FIG. 10 is a cross sectional view taken along line 10-10 of FIG. 9.

DETAILED DESCRIPTION

Figure 1:
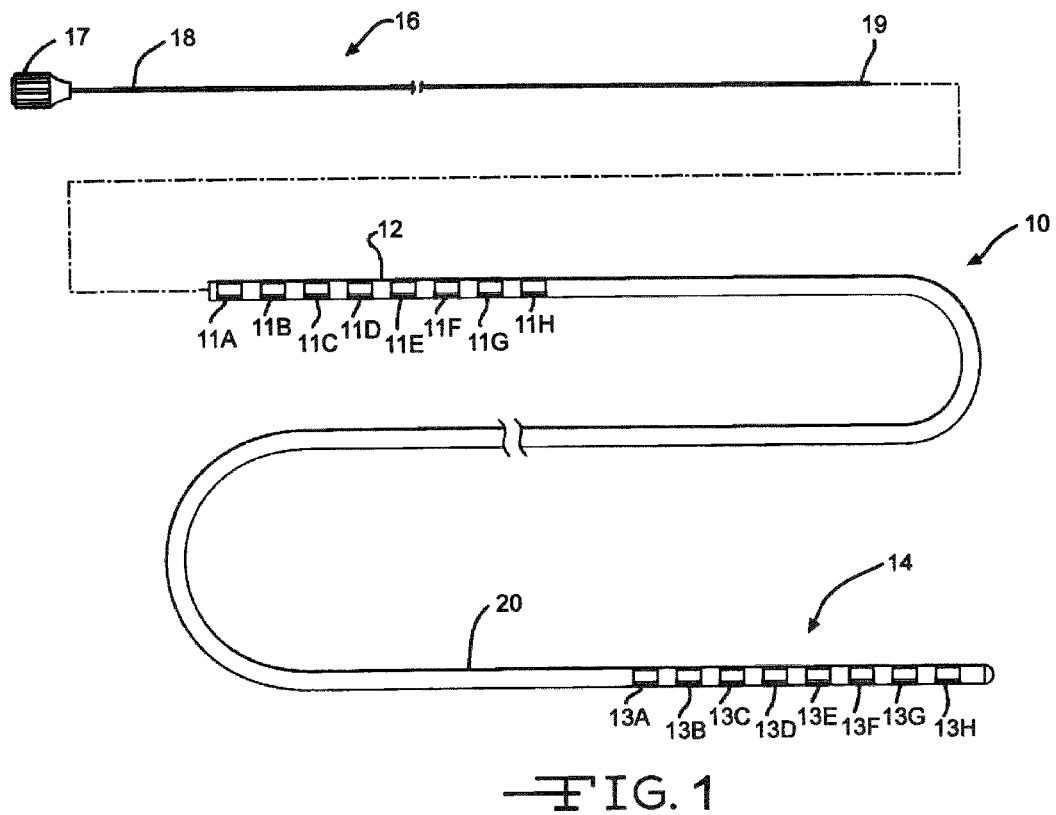
FIG. 1 illustrates a perspective view of the present invention which includes an implantable electrical stimulation lead, a lead body, electrode ring and an insertion tool.

FIG. 1 illustrates an electrical stimulation lead 10 according to the present invention for delivering therapeutic electrical stimulation. The stimulation lead 10 comprises a proximal portion 12 and a distal portion 14. Within the proximal portion 12 and the distal portion 14, respectively electrode rings 11A-11H and 13A-13H are attached to the outer surface of the polymer lead body 20. The lead body 20 is comprised of polyurethane polymer. The lead body 20 can also be comprised of alternate materials such as silicone, polyethylene, polyimide, PEEK and other biocompatible and biostable polymeric materials.

Each of the electrode rings 11A-11H and 13A-13H has an annular shape extending 360° around the outside surface of the stimulation lead body 20. Although eight electrode rings are depicted in both proximal portion and distal portions 12, 14 of FIG. 1, the number of electrode rings could range from one to as many as about thirty six or more depending on the length of the stimulation lead, the width of the electrode rings and the spacing between adjacent rings. However, the number of electrodes in the proximal portion 12 should equal the number of electrodes in the distal portion 14. That is because an internal conductor wire is attached to one of the proximal electrode rings 11A-11H and a corresponding distal electrode ring 13A-13H.

Each of the electrode rings is connected to a conductor which is preferably in a wire form. The conductor wire is preferably composed of an insulated stainless steel wire. Alternate conductor wires include insulated platinum, platinum alloy, MP35N, titanium, silver, gold, palladium or nickel alloy. The insulated conductor wire should be of about the length of the electrical stimulator lead 10 and of a diameter that fits freely with multiple insulated conductor wires inside the hollow lead body 20. A preferred conductor wire diameter is about 0.1 mm and can range from about 0.025 mm to about 0.25 mm. The insulated is preferably round, however the conductor wire can also be flat or in a cable form.

The length of the stimulation lead 10 can range from about 10 cm to about 110 cm with a preferred length of about 50 cm. The diameter of the stimulation lead 10 can range from about 0.025 cm to about 0.50 cm, with a preferred nominal diameter of about 0.127 cm. The length of an individual electrode has a range of about 0.05 mm to about 1 mm with a preferred length of about 0.118 mm. The diameter of the electrode should range about 0.025 cm to about 0.50 cm with a preferred diameter of 0.127 cm. The electrode ring should form a tight fit over the polymer lead body 20. As will be described in greater detail hereinafter, each individual electrode conductor wire assembly should be swaged to an electrode as such that the inside surface of the electrode makes contact with the conductor wire. In the exemplar, the swaged diameter of the lead is about 0.127 cm.

The stimulation lead requires a stimulation lead insertion tool or stylet 16 as depicted in FIG. 1. The lead insertion tool 16 comprises a handle 17, a proximal portion 18 and distal portion 19. The distal insertion tool portion 19 is inserted into the proximal portion of the lead 12 and advanced towards the distal portion 14 of the lead. Prior to the inserting the insertion tool, a polymer lumen is placed inside the hollow lead body to ensure the advancement of the insertion tool is unimpeded. Additionally the conductor wires can also be braided as to provide a passage way through the braided wires or move the conductor wires out of the way of the advancing insertion tool. The stimulation lead insertion tool is designed to provide a means to stiffen the stimulation lead when inserted and advanced in the body. Stimulation insertion tools are not novel but one is required in order to accurately advance and position the present stimulation lead in the body. The tubular body of the insertion tool should be composed of a rigid material such as a metal or rigid polymer. The length of the insertion tool should be about the same as that of the stimulation lead while its width is sized to fit inside that of the stimulation lead opening of about 0.03 cm to about 0.50 cm.

Figure 2:
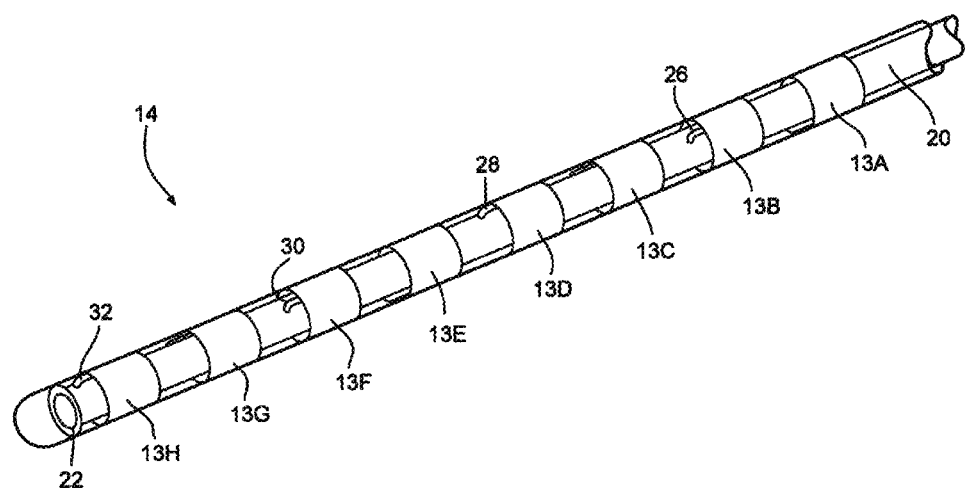
FIG. 2 depicts a perspective view of the distal portion of the present invention lead including electrode rings and respective conductor wires.

FIG. 2 illustrates an enlarged view of the distal portion 14 of the stimulation lead 10. As the illustration shows, the body of the stimulation lead extends from the proximal portion 12 to the distal portion 14 and consists of a series of electrodes that have an annular extent of about 360° about the polymeric surface lead body 20. These electrodes or electrode rings 13A-13H are composed preferably of 90/10 platinum iridium alloy. However alternate materials such as gold, platinum, additional platinum-iridium alloys, palladium, titanium, stainless steel, MP35N and other biocompatible materials can also be used. The electrode rings are periodically spaced apart from each other at about 0.5 mm to 10 mm with a preference of about 5 mm spacing.

Extending out of the polymeric body of the stimulation lead are the lead conductor wires 26, 28, 30 and 32. Each of the conductor wires 26, 28, 30, and 32, which originate from one of the proximal electrode ring electrodes 11A-11H and extend toward the distal portion of the lead 14, protrude through the wall of the polymer lead body 20 adjacent one of the distal ring electrodes 13A to 13H. In the exemplar illustration, the conductor wires protrude through the polymer lead body 20 on the distal side of the associated electrode ring. However the lead could be designed such that the conductor wires protrude through the wall of the lead body at a proximal side of the electrode. Each of the conductor wires can protrude through the polymer lead wall at any point about the 360° annular wall surface.

The proximal portion 12 of the stimulation lead is constructed in the same manner and design as that of the distal portion 14. In that respect, the proximal portion 12 consists of electrode rings 11A-11H that form a 360° annular extension about the polymeric lead body 20. The electrodes or electrode rings 11A-11H are composed preferably of 90/10 platinum iridium. However alternate materials such as gold, platinum, additional platinum iridium alloys palladium, titanium, stainless steel, MP35N and other biocompatible materials can also be used. The electrode rings are periodically spaced from each other at about 0.5 mm to 10 mm with a preference of about 5 mm spacing. Extending out of the polymeric body of the stimulation lead are the lead conductor wires.

Each of the conductor wires are first attached to the proximal portion electrodes and then extend toward the distal portion of the lead 14. Proximal portion 12 conductor wires protrude through the wall of the polymer lead body 20 on either the proximal or distal side of the electrode ring. Each of the conductor wires can protrude through the polymer lead wall at any point along the 360° annular extension. However the stimulation lead designer may use a number of electrode rings ranging from one electrode ring to as many as thirty six or more electrode rings. Although the width and spacing of the electrode rings may differ between the proximal 12 and distal 14 portions, the number of electrodes at the proximal and distal portion 12 and 14 is preferably equal.

Figure 3:
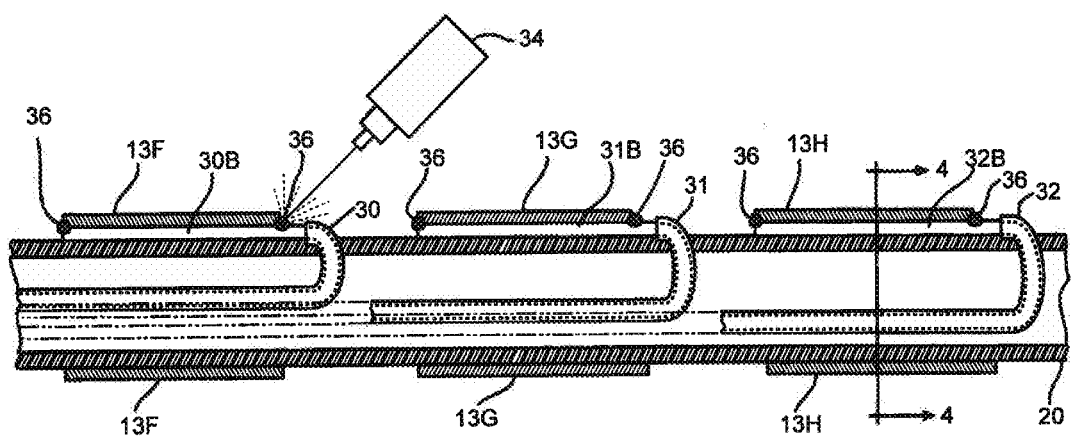
FIG. 3 illustrates a cross sectional view of the prior art of welding an electrode ring to a conductor wire.

As previously mentioned, the focus of the invention is a stimulation lead design that has an improved long term electrical connection between the conductor wire and electrode. FIG. 3 illustrates one embodiment of a prior art stimulation lead design in which welding is used to connect the conductor wire to the electrode ring. Insulated conductor wires 30, 31 and 32 advance through the hollow lumen of the lead and protrude through the polymer lumen wall 20. The insulation of the conductor wires is removed on the end portion of the wire so as to provide contact between the conductor wire 30B, 31B and 32B and the electrode ring 13F, 13G and 13H. A weld spot 36 is formed using a resistance or laser welding instrument 34 were the non-insulated conductor wire meets the edge of the electrode ring. A bond between electrode ring 13F-13H and its corresponding non-insulated portion of the conductor wire 30B-31B is thereby created at the weld 36. As previously mentioned, drawbacks to the welding process include a limited set of usable materials. Also, the welding process can expose the material of the conductor wire, which results in degradation of the electrical connection in the lead over time.

Figure 4:
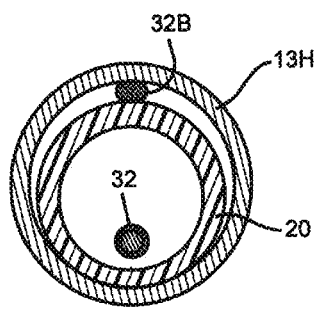
FIG. 4 illustrates a cross sectional view taken along line 3-3 of FIG. 3.

FIG. 4 depicts the hollow polymer lumen provided by the lead body 20. The insulated conductor wire 32 resides inside the hollow lumen while the bare conductor wire portion 32B has a majority of its length positioned laying on top of the lead body 20 and underneath the electrode 13H. Electrode 13H extends 360° annularly around the polymer lumen.

Figure 5:
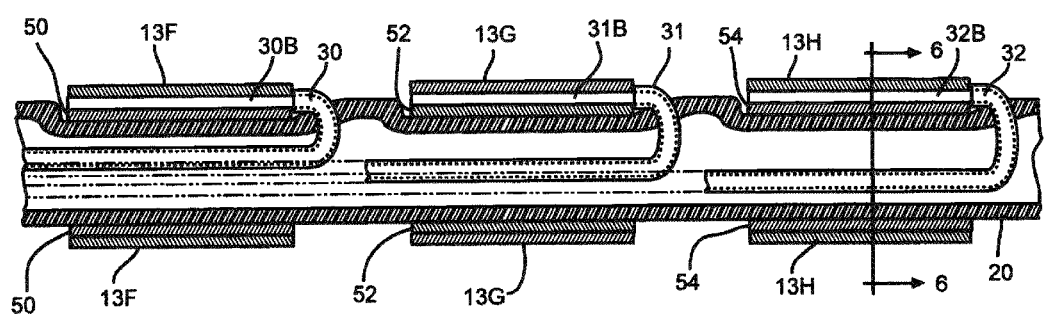
FIG. 5 depicts a cross sectional view, partially in elevation, showing electrode rings crimped to their respective conductor wires.
Figure 6:
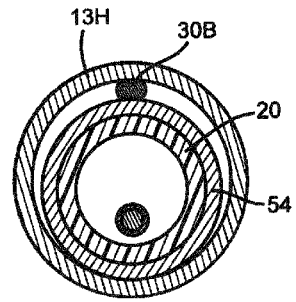
FIG. 6 illustrates a cross sectional view taken along line 6-6 of FIG. 5.

FIGS. 5 and 6 illustrate another embodiment of lead design according to the prior art. Insulated conductor wires 30, 31 and 32 are tunneled from the proximal lead portion 12 to the distal lead portion 14 through the hollow mid section of the polymer lead body 20. As each of the insulated conductor wires reach the area of their respective electrode, the wire protrudes through the wall of polymer lead body 20. Once the wire has penetrated through the lead body wall, the insulation at the end portion 30B, 31B and 32B of the wire is removed. The length of insulation that is removed is about equal to the length of the electrode ring. Metal inserts 50, 52 and 54, such as stainless steel, are first tightly fitted over the polymer lead body 20 in the area of intended placement of the electrode rings. Electrode rings 13F-13H are then fitted over the metal inserts 50, 52 and 54. The non-insulated portion of the conductor wires 30B, 31B and 32B is inserted between a respective one of the metal inserts 50, 52 and 54 and one of the electrode rings 13F-13H. Once the wire is inserted, the electrode ring, conductive wire and metal insert assembly is crimped together. However as previously mentioned, this prior art crimping method using a metal insert positioned intermediate the electrode ring and the lead body increases the width of the stimulation lead.

In that light, FIG. 7 illustrates an improved lead construction according to the present invention. The metal inserts 50, 52 and 54 of the prior art crimping method illustrates in FIGS. 5 and 6 have been removed and replaced with metal coils 70, 72 and 74, incorporated within the wall of the polymer lead body 20. The metal coils 70, 72 and 74 which are wires in a spiral formation, are incorporated in the wall of the polymer lumen in an area under electrode rings 13F-13H. These metal coils serve as a localized stiffening mechanisms in the area underneath the electrode ring as well as providing pressure points that secure the conductor wire portion 30B, 31B and 32B in place and prevent migration of polymer material of the lead lumen due to cold flow. The length of each of the coils in the exemplar should be about the same as the electrode ring. However in a different embodiment the embedded coil can extend the entire length of the distal and proximal lead portions or can span the entire length of the lead lumen 20.

The coils are formed from spiraled wire of a diameter of about 0.1 mm with a preferred spiral spacing of about 0.01 mm. However, the spacing of the coil wires can range from about 0 mm to about 0.5 mm. Stainless steel is the preferred material for composition of the embedded coils 70, 72 and 74, however, materials such as MP35N and titanium or other biocompatible rigid material such as a biocompatible rigid metal or polymer can also be used. Preferably the shape of coil wire is round, however, the wire can be flat or rectangular ribbon or diamond shaped. Each coil extends annularly 360° within the wall of the lead polymer lumen. Preferably a coil is present at each electrode ring, both in the proximal 12 and distal 14 portions of the lead. For example, if the stimulation lead has eight electrode rings in the proximal portion 12 and eight electrodes in the distal portion 14 of the lead, there would be eight metal coils in the proximal portion 12 and eight coils in the distal portion 14. The portion of the conductor wires 30, 31 and 32 that protrude through the wall of the polymer lead body are placed between the inner surface of the electrode rings 13F-13H and the surface of the polymer lead body which has the metal coils 70, 72 and 74 incorporated beneath. In the present invention, the insulation on the conductor wire underneath the electrode ring 30B, 31B and 32B can either be removed as shown in FIG. 7 or it can remain on the conductor wire. In any event, a secure connection between a conductor wire positioned intermediate one of the electrode rings and a coil reinforced section of the lead body wall is done by a swaging operation, and the like. During swaging, the metal coils 70, 72 and 74 provide pressure points that "bite" into the insulated conductor wire and make physical contact with the metallic conductor wire. The combination of the force of swaging and pressure points created by the embedded coil split away the conductor insulation. This improved design eliminates the need for metal inserts, thereby reducing the width of the stimulation lead.

The cross sectional view of FIG. 8 illustrates the metal coil 74 embedded in the wall of the polymer lumen 20 beneath the electrode ring 13H and the protruding portion 32B of the conductor wire 32. The insulated conductor wire 32 along with the other insulated conductor wires (not numbered in FIG. 8) of the stimulation lead are shown in the hollow space of the lead lumen 20. In the exemplary embodiment, eight insulated conductor wires are shown coming from the proximal portion 12. The number of insulated conductor wires in the hollow space of the polymer lead lumen 20 would be equal to the number of electrode rings at the proximal and distal portions 12 and 14.

FIG. 9 illustrates an enlarged cross sectional view of the distal lead portion 14 in the area of electrode ring 13H. As the illustration shows, the length of the protruding portion 32B of the conductor wire 32 is about the same length as that of the electrode ring 13H. That's because the electrode ring 13H is positioned immediately adjacent to where the conductor portion 32B protrudes through the wall of the lead body. The subsequent swaging operation only bites into that portion of the insulation 25 underneath the electrode. The very minor portion of the conductor wire 32 that protrudes from the wall of the lead body, but does not reside underneath the electrode ring 13H is still provided with its insulating cover 25. In fact, the insulation 25 is fluid-tight on the conductor wire to the edge 13Ha of the electrode. The conductor wire portion 32B under the electrode ring 13H should not extend past the opposite edge 13Hb of the electrode ring.

FIG. 10 shows the tight compression of the protruding portion of the conductor wire 32B in contact with the electrode ring 13H and with the metal coil 74 biting into the insulation 25 of the 32B. This is shown in the cross section of FIG. 10 where the physical deformation of the electrode 13H brought about by the swaging operation has penetrated or bit through the insulation 25 surrounding the protruding portion 32B of wire 32 to make direct physical contact between the electrode 13H and the metal of the protruding portion 32B of the conductor. This figure also shows that the coil 74 has bit into the insulation 25 to make direct physical contact with the protruding portion 32B of the conductor. However, that is not necessary for a properly functioning lead. All that is required is for the electrode 13H to make direct physical contact with the protruding portion 32B of the conductor 32.

Some aspects of some examples and embodiments of the present invention have been discussed in the specification. The scope of the invention is given in the claims which follow.

What is claimed is:

1. An implantable medical electrical lead, which comprises:
    a) an elongate lead body comprising a sidewall surrounding a lumen having a length extending from a proximal lead portion to a distal lead portion;
    b) at least one coil disposed in the lead body sidewall surrounding the lumen;
    c) at least one proximal electrode disposed in the proximal lead portion;
    d) at least one distal electrode disposed in the distal lead portion;
    e) at least one wire of an electrically conductive metal disposed along the length of the lead body to provide electrical continuity from the proximal electrode to the distal electrode, wherein at least one of the proximal and distal electrodes is spaced radially outwardly from at least a portion of the coil and a portion of the lead wire protrudes through the lead body sidewall and resides between the at least one of the proximal and distal electrodes and the coil; and
    f) wherein the at least one of the proximal and distal electrodes contacts the protruding portion of the wire.

2. The lead of claim 1 wherein the at least one of the proximal and distal electrodes is characterized as having been physically deformed into a direct contact relationship with the metal of the protruding portion of the wire.

3. The lead of claim 1 wherein the protruding portion of the wire is in a direct contact relationship with the coil.

4. The lead of claim 1 wherein the coil is a spiral member that is embedded in the sidewall of the lead body.

5. The lead of claim 1 wherein the coil is disposed in both the proximal lead portion and the distal lead portion.

6. The lead of claim 1 wherein the at least one of the proximal and distal electrode is an annular member surrounding the sidewall of the lead body.

7. The lead of claim 2 wherein a length of the protruding portion of the wire in direct contact relationship with the electrode is substantially equal to a length of the electrode.

8. The lead of claim 3 wherein a length of the coil in direct contact relationship with the protruding wire portion is substantially equal to a length of the electrode.

9. The lead of claim 1 wherein there are a plurality of proximal electrodes and a like number of distal electrodes.

10. The lead of claim 9 wherein there are a like number of wires as proximal electrodes and distal electrodes, one such wire being in electrical continuity from one of the proximal electrodes to one of the distal electrodes.

11. The lead of claim 10 wherein a proximal electrode is characterized as having been deformed into a direct contact relationship with the metal of a proximal protruding portion of the wire and wherein a distal electrode is characterized as having been deformed into a direct contact relationship with the metal of a distal protruding portion of the wire.

12. The lead of claim 11 wherein the proximal protruding portion of the wire is characterized as having been deformed into a direct contact relationship with the coil and the distal protruding portion of the wire is characterized as having been deformed into a direct contact relationship with the coil.

13. The lead of claim 12 wherein the coil in direct contact relationship with the proximal protruding portion of the wire and the coil in direct contact relationship with the distal protruding portion of the wire are distinct first and second coils.

14. The lead of claim 12 wherein the coil in direct contact relationship with the proximal protruding portion of the wire and the coil in direct contact relationship with the distal protruding portion of the wire are portions of the same coil.

15. The lead of claim 1 wherein the metal of the wire is selected from the group consisting of stainless steel wire, platinum, platinum alloy, MP35N, titanium, silver, gold, palladium and nickel.

16. The lead of claim 1 wherein the electrode is selected from the group consisting of platinum/iridium alloy, gold, platinum, palladium, titanium, stainless steel, and MP35N alloy.

17. The lead of claim 1 wherein the coil is composed of a material selected from the group consisting of stainless steel, MP35N, titanium, and a polymer.

18. The lead of claim 1 wherein the wire resides in the lumen for a substantial portion of the length of the wire.

19. The claim of claim 1 wherein the coil wire can be round, flat, diamond shaped.

20. An implantable medical electrical lead, which comprises:
    a) an elongate lead body comprising a sidewall surrounding a lumen having a length extending from a proximal lead portion to a distal lead portion;
    b) at least one coil disposed in the lead body sidewall surrounding the lumen;
    c) at least one proximal electrode disposed in the proximal lead portion;
    d) at least one distal electrode disposed in the distal lead portion;
    e) at least one wire of an electrically conductive metal disposed along the length of the lead body to provide electrical continuity from the proximal electrode to the distal electrode, wherein at least one of the proximal and distal electrodes is spaced radially outwardly from at least a portion of the coil and a portion of the lead wire protrudes through the lead body sidewall and resides between the at least one of the proximal and distal electrodes and the coil; and
    f) wherein the at least one of the proximal and distal electrodes contacts the protruding portion of the wire and the protruding portion of the wire is characterized as having been deformed into a direct contact relationship with the coil.

21. A method for providing an implantable medical electrical lead, comprising the steps of:
    a) providing an elongate lead body comprising a sidewall surrounding a lumen having a length extending from a proximal lead portion to a distal lead portion with at least one coil disposed in the lead body sidewall surrounding the lumen;
    b) providing at least one proximal electrode in the proximal lead portion and at least one distal electrode in the distal lead portion, wherein at least one of the proximal and distal electrodes is spaced radially outwardly from at least a portion of the coil;

c) providing at least one wire of an electrically conductive metal extending along the length of the lead body with a portion of the lead wire protruding through the lead body sidewall and residing between the at least one of the proximal and distal electrodes and the coil; and
d) providing the at least one of the proximal and distal electrodes into contact with the protruding portion of the wire.

22. The method of claim 21 including providing the at least one of the proximal and distal electrodes into direct physical contact with the metal of the protruding portion of the wire.

23. The method of claim 21 including swaging the at least one of the proximal and distal electrodes into direct physical contact with the metal comprising the protruding portion of the wire.

24. The method of claim 21 including providing the protruding portion of the wire in a direct contact relationship with the coil.

25. The method of claim 21 including providing the coil being disposed in both the proximal lead portion and the distal lead portion.

26. The method of claim 21 including providing a length of the protruding portion of the wire in direct contact with the electrode being substantially equal to a length of the electrode.

27. The method of claim 24 including providing a length of the coil in direct contact with the protruding wire portion being substantially equal to a length of the electrode.

28. The method of claim 21 including providing a plurality of proximal electrodes and a like number of distal electrodes with a like number of wires as proximal electrodes and distal electrodes, one such wire being in electrical continuity from one of the proximal electrodes to one of the distal electrodes.

29. The method of claim 21 including selecting the metal of the wire from the group consisting of stainless steel wire, platinum, platinum alloy, MP35N, titanium, silver, gold, palladium and nickel and selecting the electrode from the group consisting of platinum/iridium alloy, gold, platinum, palladium, titanium, stainless steel, and MP35N alloy.

* * * * *